United States Patent
Böttcher et al.

Patent Number: 5,256,673
Date of Patent: Oct. 26, 1993

[54] INDOLE-3-YL-A-TETRAHYDROPYRIDYL OR PIPERIDYL COMPOUNDS

[75] Inventors: Henning Böttcher, Darmstadt; Hans-Heinrich Hausberg, Ober-Ramstadt; Christoph Seyfried, Seeheim-Jugenheim; Klaus-Otto Minck, Ober-Ramstadt, all of Fed. Rep. of Germany

[73] Assignee: Merck Patent Gesellschaft mit beschränkter Haftung, Darmstadt, Fed. Rep. of Germany

[21] Appl. No.: 377,343

[22] Filed: Jul. 10, 1989

Related U.S. Application Data

[63] Continuation-in-part of Ser. No. 674,635, Nov. 26, 1984, abandoned.

Foreign Application Priority Data

Nov. 25, 1983 [DE] Fed. Rep. of Germany ....... 3342632

[51] Int. Cl.$^5$ .................. C07D 401/06; A61K 31/44
[52] U.S. Cl. .................. 514/338; 514/339; 514/321; 514/323; 546/197; 546/201; 546/270; 546/273
[58] Field of Search ............ 546/201, 197, 270, 273; 514/338, 339, 321, 323

References Cited

U.S. PATENT DOCUMENTS

| | | | |
|---|---|---|---|
| 3,639,414 | 2/1972 | Aicher | 546/273 |
| 4,251,538 | 2/1981 | Hausberg et al. | 546/273 |
| 4,460,594 | 7/1984 | Markwell | 546/147 |

*Primary Examiner*—Jane T. Fan
*Attorney, Agent, or Firm*—Millen, White, Zelano, & Branigan

[57] ABSTRACT

Indole derivatives of the general formula I

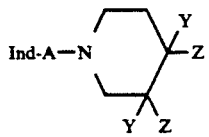

wherein
Ind is an indol-3-yl radical which is substituted by a hydroxymethyl or COW group and can additionally be monosubstituted or disubstituted by alkyl, O-alkyl, OH, F, Cl or Br,
W is H, OH, Oalkyl, $NH_2$, NHalkyl or N(alkyl)$_2$,
A is —$(CH_2)_n$—, $CH_2$—S—$CH_2CH_2$—, —$CH_2$—SO—$CH_2CH_2$ or —$CH_2$—$SO_2$—$CH_2CH_2$,
n is 2, 3, 4 or 5,
the two radicals Y are each H or together are a C—C bond, one radical Z is Ar,
the other radical Z is H and
Ar is a phenyl group which is unsubstituted or monosubstituted or disubstituted by O-alkyl and/or OH or is substituted by a methylenedioxy group, or Ar is a 2-thienyl or 3-thienyl group,
the alkyl groups each having 1-4 C atoms,
wherein, however, when n is 2 or 3, the hydroxymethyl or COW group must be in the 4-, 5-, 6- or 7-position of the indol-3-yl radical,
and physiologically acceptable acid addition salts thereof exhibit an action on the central nervous system.

11 Claims, No Drawings

INDOLE-3-YL-A-TETRAHYDROPYRIDYL OR PIPERIDYL COMPOUNDS

CROSS REFERENCE TO RELATED APPLICATIONS

This application is a continuation-in-part of application Ser. No. 674,635, filed Nov. 26, 1984 now abandoned.

This application is related to commonly assigned application Ser. No. 537,621 of Sep. 30, 1983; 572,280 of Jan. 20, 1984; and Ser. No. 588,406 of Mar. 12, 1984.

This application relates to new indole derivatives having valuable pharmacological activity.

SUMMARY OF THE INVENTION

It is an object of this invention to provide new compounds having pharmacological activity and being useful for preparation of medicaments.

Upon further study of the specification and appended claims, further objects and advantages of this invention will become apparent to those skilled in the art.

These objects have been achieved by providing new indole derivatives of the formula I

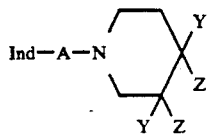

wherein

Ind is an indol-3-yl radical which is substituted by a hydroxymethyl or COW group and which can additionally be monosubstituted or disubstituted by alkyl, O-alkyl, OH, F, Cl or Br, W is H, OH, Oalkyl, $NH_2$, NHalkyl or $N(alkyl)_2$, A is $-(CH_2)n-$, $-CH_2-S-CH_2CH_2-$, $-CH_2-SO-CH_2CH_2-$ or $-CH_2-SO_2-CH_2CH_2-$, n is 2, 3, 4 or 5, the two radicals Y are each H or together are a C—C bond, one radical Z is Ar, the other radical Z is H and Ar is a phenyl group which is unsubstituted or is monosubstituted or disubstituted by O-alkyl and/or OH or is substituted by a methylenedioxy group, or Ar is a 2-thienyl or 3-thienyl group, in which formula each of the alkyl groups has 1–4 C atoms, wherein, however, when n is 2 or 3, the hydroxymethyl or COW group must be in the 4-, 5-, 6- or 7-position of the indol-3-yl radical.

and also physiologically acceptable acid addition salts thereof.

DETAILED DISCUSSION

It has been found that the compounds of the formula I and their physiologically acceptable acid addition salts possess valuable pharmacological properties. Thus, they exhibit, in particular, an action on the central nervous system, above all a dopamine-stimulating presynaptic (neuroleptic) or postsynaptic (anti-Parkinsonian) action. In detail, the compounds of the formula I induce contralateral turning behavior in hemiparkinson rats (detectable by the method of Ungerstedt et al., Brain Res. 24 (1970), 485–493) and inhibit the binding of tritiated dopamine-agonists and dopamine-antagonists to striatal receptors (detectable by the method of Schwarcz et al., J. Neuro-Chemistry 34 (1980), 772–778 and Creese et al., European J. Pharmacol. 46 (1977), 377–381). In addition, the compounds inhibit the linguomadibular reflex in anaesthetized rats (detectable by a method based on the methods of Barnett et al., European J. Pharmacol. 21 (1973), 178–182 and of Ilhan et al., European J. Pharmacol. 33 (1975), 61–64). Analgesic and hypotensive effects also occur; thus in conscious, catheter-carrying, naturally hypertensive rats (strain SHR/NIH-MO/CHB-EMD; for method see Weeks and Jones, Proc. Soc. Exptl. Biol. Med. 104 (1960), 646–648), the directly measured blood pressure is lowered after intragastric administration of the compounds.

Compounds of the formula I and their physiologically acceptable acid addition salts can, therefore, be used as active compounds for medicaments and also as intermediate products for the preparation of other active compounds for medicaments.

In the radicals Ind, W and Ar, alkyl is preferably methyl and also ethyl, n-propyl, isopropyl, n-butyl, isobutyl, sec.-butyl or tert.-butyl. O-Alkyl is preferably methoxy, and also ethoxy, n-propoxy, isopropoxy, n-butoxy, isobutoxy, sec.-butoxy or tert.-butoxy.

The radical Ind is, in particular, a monosubstituted indol-3-yl radical. It is preferably substituted in the 5-position or 6-position or in the 4-position or 7-position. Substitution in the 1-position or 2-position is also possible. Preferred disubstituted indol-3-yl radicals are substituted in the 5,6-position; disubstitution is also possible in the 1,2-, 1,4-, 1,5-, 1,6-, 1,7-, 2,4-, 2,5-, 2,6-, 2,7-, 4,5-, 4,6-, 4,7-, 5,7- or 6,7-position. In all these cases the substituents can be identical or different.

Specifically, the preferred substituents in the benzene ring of the radical Ind are hydroxymethyl, formyl, carboxyl, methoxycarbonyl, ethoxycarbonyl, carbamoyl, N-methylcarbamoyl, N-ethylcarbamoyl, N,N-dimethylcarbamoyl or N,N-diethylcarbamoyl; in the second place they are propoxycarbonyl, isopropoxycarbonyl, butoxycarbonyl, isobutoxycarbonyl, sec.-butoxycarbonyl and tert.-butoxycarbonyl, N-propylcarbamoyl, N-isopropylcarbamoyl, N-butylcarbamoyl, N-isobutylcarbamoyl, N-sec.-butylcarbamoyl, N-tert.-butylcarbamoyl, N-methyl-N-ethylcarbamoyl, N,N-dipropylcarbamoyl, N-methyl-N-propylcarbamoyl, N-ethyl-N-propylcarbamoyl and N,N-dibutylcarbamoyl and, additionally, methyl, ethyl, methoxy, ethoxy, OH, F, Cl and/or Br. Accordingly, some preferred meanings of the radical Ind are 2-, 4-, 5-, 6- or 7-formylindol-3-yl, 2-, 4-, 5-, 6- or 7-carboxyindol-3-yl, 2-, 4-, 5-, 6- or 7-methoxycarbonylindol-3-yl, 2-, 4-, 5-, 6- or 7-ethoxycarbonylindol-3-yl, 2-, 4-, 5-, 6- or 7-carbamoylindol-3-yl, 2-, 4-, 5-, 6- or 7-N-methylcarbamoylindol3-yl, 2-, 4-, 5-, 6- or 7-N-ethylcarbamoylindol-3yl, 2-, 4-, 5-, 6- or 7-N,N-dimethylcarbamoylindol-3-yl, 2-, 4-, 5-, 6- or 7-N,N-diethylcarbamoylindol-3-yl, 1-methyl-4-, -5-, -6- or -7-hydroxymethylindol-3-yl, 1-methyl-4-, -5-, -6- or -7-formylindol-3-yl, 1-methyl-4-, -5-, -6- or -7-carboxyindol-3yl, 1-methyl-4-, -5-, -6- or -7-carbamoylindol-3-yl, 2-methyl-4-, -5-, -6- or -7-hydroxymethylindol-3yl, 2-methyl-4-, -5-, -6- or -7-formylindol-3-yl, 2-methyl-4-, -5-, -6- or -7-carboxyindol-3-yl, 2-methyl-4-, -5-, -6- or -7-carbamoylindol-3-yl, 5-methoxy-4-, -6- or -7-methoxycarbonylindol-3-yl, 5-methoxy-4-, -6- or -7-ethoxycarbonylindol-3-yl, 5-methoxy-4-, -6- or -7-carboxyindol-3-yl, 5-methoxy-4-, -6- or -7-carbamoylindol-3-yl, 5- fluoro-4-, -6- or -7-carboxyindol-3-yl, 5-chloro-4-, -6- or -7-carboxyindol-3-yl, 7-chloro-4-, -5- or -6-carboxyindol-3-yl, 5-bromo-4-, -6- or -7-carboxyindol-3-yl, 5-hydroxy-4-, -6- or -7-methoxycarbonylindol-3-yl, 5-hydroxy-4-, -6- or -7-ethoxycarbonylindol-3-yl, 5-hydroxy-4-, -6- or -7-carboxyindol-3-yl, 5-hydroxy-4-, -6- or -7-carbamoylindol-3-yl, 5-hydroxy-2-, -4-, -6- or -7-hydroxymethylindol-3-yl, 6-hydroxy-4-, -5- or -7-carboxyindol-3-yl, 6-hydroxy-2-, -4-, -5- or -7-hydroxymethylindol-3-yl.

The parameter n is preferably 4 and the radical A is preferably —(CH$_2$)$_4$— or —CH$_2$—S—CH$_2$CH$_2$— and also preferably —(CH$_2$)$_2$—, —(CH$_2$)$_3$— or —(CH$_2$)$_5$—.

The radical Ar is preferably unsubstituted phenyl. If Ar is a substituted phenyl group, the latter is preferably monosubstituted. It can, however, also be disubstituted, and the substituents can be identical or different. Preferred substituents on the phenyl group are methoxy and OH. Specifically, Ar is preferably phenyl, o-, m- or p-methoxyphenyl, o-, m- or p-hydroxyphenyl and also o-, m- or p-ethoxyphenyl, 2,3-, 2,4-, 2,5-, 2,6-, 3,4- or 3,5-dimethoxyphenyl, 3-hydroxy-4-methoxyphenyl, 3-methoxy-4-hydroxyphenyl, 2,3-, 2,4-, 2,5-, 2,6-, 3,4- or 3,5-dihydroxyphenyl, 2,3- or 3,4-methylenedioxyphenyl, 2-thienyl or 3-thienyl.

Accordingly, the invention relates especially to the compounds of the formula I in which at least one of the said radicals has one of the meanings indicated above, particularly the preferred meanings indicated above. Some preferred groups of compounds can be expressed by means of the following partial formulae Ia to Ik, which correspond to the formula I and in which the radicals and parameters not designated in detail have the meaning indicated in formula I, but in which:

in Ia Ind is hydroxymethylindol-3-yl, formylindol-3-yl, carboxyindol-3-yl, methoxycarbonylindol-3-yl, ethoxycarbonylindol-3-yl, carbamoylindol-3-yl, ethoxycarbonylmethoxyindol-3-yl or carboxymethoxyindol-3-yl, the substituents being preferably in the 5-position and/or 6-position;

In Ib Ind is 4-, 5-, 6- or 7-hydroxymethylindol-3-yl, 5-, 6- or 7-formylindol-3-yl, 5-, 6- or 7-carboxyindol-3-yl, 5-, 6- or 7-methoxycarbonylindol-3-yl, 5-, 6- or 7-ethoxycarbonylindol-3-yl, 5-, 6- or 7-carbamoylindol-3-yl, 5-methoxy-6-ethoxycarbonylindol-3-yl or 5-methoxy-6-carboxyindol-3-yl;

in Ic A is —(CH$_2$)$_n$— or —CH$_2$—S—CH$_2$CH$_2$—;
in Id A is —(CH$_2$)$_4$—;
in Ie the two radicals Y are together a C—C bond;
in If Ar is phenyl, hydroxyphenyl or methoxyphenyl;
in Ig Ar is in the 4-position and is phenyl;
in Ih Ind is 4-, 5-, 6- or 7-hydroxymethylindol-3-yl, 5-, 6- or 7-formylindol-3-yl, 5-, 6- or 7-carboxyindol-3-yl, 5-, 6- or 7-methoxycarbonylindol-3-yl, 5-, 6- or 7-ethoxycarbonylindol-3-yl, 5-, 6- or 7-carbamoylindol-3-yl, 5-methoxy-6-ethoxycarbonylindol-3-yl or 5-methoxy-6-carboxyindol-3yl, A is —(CH$_2$)$_n$— or —CH$_2$—S—CH$_2$CH$_2$— and Ar is phenyl, hydroxyphenyl or methoxyphenyl;

in Ii Ind is 4-, 5-, 6- or 7-hydroxymethylindol-3-yl, 5-, 6- or 7-formylindol-3-yl, 5-, 6- or 7-carboxyindol-3-yl, 5-, 6- or 7-methoxycarbonylindol-3-yl, 5-, 6- or 7-ethoxycarbonylindol-3-yl, 5-, 6- or 7-carbamoylindol-3-yl, 5-methoxy-6-ethoxycarbonylindol-3-yl or 5-methoxy-6-carboxyindol-3-yl, A is —(CH$_2$)$_4$— or —CH$_2$—S—CH$_2$CH$_2$— and Ar is phenyl, m-hydroxyphenyl or p-hydroxyphenyl;

in Ij Ind is carboxyindol-3-yl or carbamoylindol-3-yl, A is —(CH$_2$)$_4$— or —CH$_2$—S—CH$_2$CH$_2$— and Ar is phenyl, m-hydroxyphenyl or p-hydroxyphenyl;

in Ik Ind is 5-carboxyindol-3yl or 5-carbamoylindol-3-yl, A is —(CH$_2$)$_4$— or —CH$_2$—S—CH$_2$CH$_2$— and the two radicals Y together are a C—C bond and Ar is in the 4-position and is phenyl.

The compounds of the formula I can contain one or more asymmetric carbon atoms. They can, therefore, exist as racemates and, if several asymmetric carbon atoms are present, also as mixtures of several racemates, as well as in different optically active forms.

The invention also relates to a process for the preparation of the compounds of the formula I and of their physiologically acceptable acid addition salts, wherein a compound of the general formula II Ind—A—X$^1$         II wherein X$^1$ is X or NH$_2$ and X is Cl, Br, I, OH or a reactive, functionally modified OH group, and Ind and A have the meanings indicated, is reacted with a compound of the general formula III

X$^2$—CH$_2$CH$_2$—CYZ—CYZ—CH$_2$—X$^3$         III wherein

X$^2$ and X$^3$ can be identical or different and, if X$^1$ is NH$_2$, are each X and otherwise are together NH and Y and Z have the meanings indicated, or a compound which otherwise corresponds to the formula I, but which contains one or more reducible group(s) and/or one or more additional C—C and/or C—N bond(s) instead of one or more hydrogen atoms, is treated with a reducing agent, or a compound which otherwise corresponds to the formula I, but which contains one or more solvolyzable group(s) instead of one or more hydrogen atoms, is treated with a solvolytic agent, or, in order to prepare thioesters of the formula I wherein A is —CH$_2$—S—CH$_2$CH$_2$—, a compound of the general formula IV Ind—CH$_2$N(R)$_2$         IV wherein R is alkyl having 1-4 C atoms or both radicals R together are also —(CH$_2$)$_p$— or —CH$_2$CH$_2$OCH$_2$CH$_2$— and p is 4 or 5 and Ind has the meaning indicated, is reacted with a thiol of the general formula V

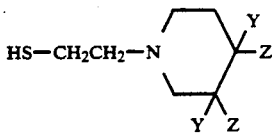

wherein

Y and Z have the meanings indicated, or with one of its salts, or, in order to prepare compounds of the formula I wherein both radicals Y together are a C—C bond, a compound of the general formula IV

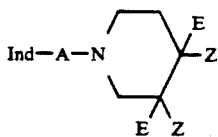

wherein
one radical E is X, CN or $NH_2$,
the other radical E is H and
Ind, A, Z and X have the meanings indicated,
is treated with an agent which splits off HE, and/or in a compound of the formula I, if appropriate, a thioether group is oxidized to give an SO group or $SO_2$ group or an SO group is oxidized to give an $SO_2$ group and/or an alkoxy group is split with the formation of an OH group and/or a COW group is converted into another COW group by oxidation, reduction, esterification, amidation or solvolysis and/or a COW group is reduced to give a hydroxymethyl group and/or a hydroxymethyl group is oxidized to give a CHO or COOH group and/or a resulting base of the formula I is converted, by treatment with an acid, into one of its physiologically acceptable acid addition salts.

The preparation of the compounds of the formula I is effected in other respects by methods which are in themselves known, such as are described in the literature (for example in the standard works, such as Houben-Weyl, Methoden der Organischen Chemie (Methods of Organic Chemistry), Georg-Thieme-Verlag, Stuttgart; or Organic Reactions, John Wiley & Sons, Inc., New York), specifically under reaction conditions such as are known and suitable for the reactions mentioned. In these reactions it is also possible to make use of variants which are in themselves known but not mentioned here in detail.

The starting materials for the claimed process can, if desired, also be formed in situ, in such a way that they are not isolated from the reaction mixture but are immediately reacted further to give the compounds of the formula I.

In the indole derivatives of the formula II, $X^1$ is preferably X; accordingly, in the compounds of the formula III, $X^2$ and $X^3$ together are preferably NH. The radical X is preferably Cl or Br; it can, however, also be I, OH or a reactive, functionally modified OH group, especially alkylsulfonyloxy having 1-6 C atoms (for example methanesulfonyloxy) or arylsulfonyloxy having 6-10 C atoms (for example benzenesulfonyloxy, p-toluenesulfonyloxy, 1-naphthalenesulfonyloxy or 2-naphthalenesulfonyloxy).

Accordingly, the indole derivatives of the formula I are obtainable, in particular, by reacting compounds of the formula Ind-A-Cl or Ind-A-Br with piperidine or tetrahydropyridine derivatives of the formula III wherein $X^2$ and $X^3$ together are an NH group (designated below as IIIa).

The compounds of the formulae II and especially III are in part known; the compounds of the formulae II and III which are not known can readily be prepared analogously to the known compounds. Compounds of the formula II (A=$-CH_2-S-CH_2CH_2-$) can be prepared, for example, from Mannich bases of the formula IV and thiols of the formula $HS-CH_2CH_2-X^1$, for example $HS-CH_2CH_2OH$. The sulfoxides sulfones of the formula II (A=$-CH_2-SO-CH_2CH_2-$ or $-CH_2-SO_2-CH_2CH_2-$) are accessible by oxidizing the thioethers (II, A=$-CH_2-S-CH_2CH_2-$). Primary alcohols of the formula Ind-A-OH can be obtained, for example, by reducing the corresponding carboxylic acids or their esters. Treatment with thionyl chloride, hydrogen bromide, phosphorus tribromide or similar halogen compounds given the corresponding halides of the formula Ind-A-Hal. The corresponding sulfonyloxy compounds can be obtained from the alcohols Ind-A-OH by reaction with the corresponding sulfonyl chlorides.

The iodine compounds of the formula Ind-A-I can be obtained, for example, by the action of potassium iodide on the appropriate p-toluenesulfonic acid esters. The amines of the formula Ind-A-$NH_2$ can be prepared, for example, from the halides by means of potassium phthalimide or by reducing the corresponding nitriles.

The piperidine derivatives IIIa are, for the most part, known (cf. German Offenlegungsschrift 2,060,816) and can be obtained, for example, by reacting 3-piperidone or 4-piperidone with organometallic compounds of the formula M-Ar (wherein M is an Li atom or MgHal), subsequently hydrolyzing the product to give the corresponding 3-Ar-3-hydroxypiperidines or 4-Ar-4-hydroxypiperidines and, if desired, subsequently dehydrating the latter to give 3-Ar-3,4-dehydropiperidines or 4-Ar-3,4-dehydropiperidines. Compounds of the formula III ($X^2$ and $X^3$ being X in each case) can be prepared, for example, by reducing diesters of the formula alkylOOC-$CH_2$-CYZ-CYZCOOalkyl to give diols of the formula HO-$CH_2CH_2$-CYZ-CYZ$CH_2$OH (III, $X^2=X^3=$OH) and, if appropriate, subsequently reacting the latter with $SOCl_2$ or $PBr_3$.

The reaction of the compounds II and III takes place in accordance with methods such as are known from the literature for the alkylation of amines. The components can be melted with one another in the absence of a solvent, if appropriate in a sealed tube or in an autoclave. It is also possible, however, to react the compounds in the presence of an inert solvent. Examples of suitable solvents are hydrocarbons, such as benzene, toluene or xylene; ketones, such as acetone or butanone; alcohols, such as methanol, ethanol, isopropanol or n-butanol; ethers, such as tetrahydrofuran (THF) or dioxane; amides, such as dimethylformamide (DMF) or N-methylpyrrolidone; nitriles, such as acetonitrile, and also, if appropriate, mixtures of these solvents with one another or mixtures with water. IT can be advantageous to add an acid-binding agent, for example an alkali metal or alkaline earth metal hydroxide, carbonate or bicarbonate or another salt of a weak acid of the alkali or alkaline earth metals, preferably the potassium, sodium or calcium salt, or to add an organic base, such as triethylamine, dimethylaniline, pyridine or quinoline, or an excess of the amine component Ind-A-$NH_2$ or of the piperidine derivative of the formula IIIa. Depending on the conditions employed, the reaction time is between a few minutes and 14 days, while the reaction temperature is between about 0° and 150°, normally between 20° and 130°.

It is also possible to obtain a compound of the formula I by treating a precursor containing one or more reducible group(s) and/or one or more additional C—C and-/or C—N bond(s) instead of hydrogen atoms with a reducing agent, preferably at temperatures between −80° and +250° and in the presence of at least one inert solvent.

Reducible groups (replaceable by hydrogen) are, in particular, oxygen in a carbonyl group, hydroxyl, arylsulfonyloxy (for example p-toluenesulfonyloxy), N-benzenesulfonyl, N-benzyl or O-benzyl.

In principle, it is possible to convert compounds containing only one of the groups or additional bonds listed above, or compounds containing two or more of the groups or additional bonds listed above, adjacent to one another, to a compound of the formula I by reduction; COW groups present in the starting compound can be reduced at the same time. For this purpose it is preferable to use nascent hydrogen or complex metal hydrides, and also the Wolff-Kishner method of reduction.

The most preferred starting materials for the reduction correspond to the formula VII

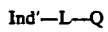     VII wherein

Ind' is an indol-3-yl radical which is substituted by a hydroxymethyl or COW group and which can, in addition, be monosubstituted or disubstituted by alkyl, O-alkyl, OH, F, Cl, Br and/or O-benzyl and/or can be substituted in the 1-position by an arylsulfonyl group or a benzyl group, L is A or a chain which corresponds to the radical A but in which one or more —$CH_2$— group(s) have been replaced by —CO— and/or one or more hydrogen atoms have been replaced by OH groups, Q is

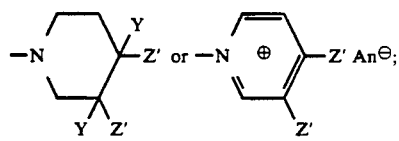

one radical Z' is Ar', the other radical Z' is H,

An⁻ is an anion of a strong acid and

Ar' is a phenyl group which is unsubstituted or is monosubstituted or disubstituted by O-alkyl, OH and/or O-benzyl or is substituted by a methylenedioxy group, but wherein it is not possible at the same time for Ind' to be Ind, L to be A, Q to be

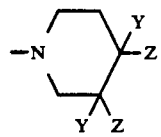

and Ar' to be Ar.

In the compounds of the formula VII, L is preferably —CO—$(CH_2)_{n-2}$—CO— [specifically —COCO—, —$COCH_2CO$—, —CO—$(CH_2)_2$—CO— or —CO—$(CH_2)_3$—CO—], —$(CH_2)_{n-1}$—CO— [specifically —$CH_2CO$—, —$CH_2CH_2$—CO—, —$(CH_2)_3$—CO— or —$(CH_2)_4$—CO—], —$CH_2$—S—$CH_2$—CO—, —$CH_2$—SO—$CH_2$—CO— or —$CH_2$—$SO_2$—$CH_2$—CO— and also, for example, —CO—$CH_2CH_2$—, —$CH_2$—CO—$CH_2$—, —CO—$(CH_2)_3$—, —$CH_2$—CO—$CH_2CH_2$—, —$CH_2CH_2$—CO—$CH_2$—, —CO—$(CH_2)_4$—, —$CH_2$—CO—$(CH_2)_3$—, —$CH_2CH_2$—CO—$CH_2CH_2$— or —$(CH_2)_3$—CO—$CH_2$—.

Compounds of the formula VII can be prepared, for example, by reacting 4-Ar'-1,2,3,6-tetrahydropyridine or 4-Ar'-pyridine with a compound of the formula VIII

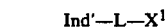     VIII wherein

Ar', Ind', L and $X^1$ have the meanings indicated above, under the conditions indicated above for the reaction of II with III.

If the reducing agent used in nascent hydrogen, the latter can be produced, for example, by treating metals with weak acids or with bases. Thus it is possible, for example, to use a mixture of zinc and an alkali metal hydroxide solution or of iron and acetic acid. It is also possible to use sodium or another alkali metal in an alcohol, such as ethanol, isopropanol, butanol, amyl alcohol or isoamyl alcohol or phenol. It is also possible to use an aluminum/nickel alloy in an aqueous alkaline solution, if appropriate with the addition of ethanol. Sodium amalgam or aluminum amalgam in an aqueous alcoholic or aqueous solution are also suitable for the production of the nascent hydrogen. The reaction can also be carried out in a heterogeneous phase, preferably using an aqueous phase and a benzene or toluene phase.

Complex metal hydrides, such as $LiAlH_4$, $NaBH_4$, diisobutylaluminum hydride or $NaAl(QCH_2CH_2OCH_3)_2H_2$ and diborane can also be employed with particular advantage as the reducing agent, if desired with the addition of catalysts, such as $BF_3$, $AlCl_3$ or LiBr. Solvents suitable for this reaction are, in particular, ethers, such as diethyl ether, di-n-butyl ether, THF, dioxane, diglyme or 1,2-dimethoxyethane, and also hydrocarbons, such as benzene. Alcohols, such as methanol or ethanol, and also water and aqueous alcohols are primarily suitable as solvent for reduction with $NaBH_4$. Reduction by these methods is preferably carried out at temperatures between −80° and +150°, in particular between about 0° and about 100°.

CO groups in acid amides or vinylogous acid amides (for example those of the formula VII wherein L is a —$(CH_2)_{n-1}$—CO—, —$CH_2$—S—$CH_2$—CO— or —CO—$(CH_2)_{n-2}$—CO— group) can be reduced to give $CH_2$ groups particularly advantageously by means of $KiAlH_4$ in THF at temperatures between about 0° and 66°. In the course of this it is possible to split off by simultaneous reduction arylsulfonyl protective groups present in the 1-position of the indole ring and/or to reduce COW groups present on the indole ring, for example to reduce COOalkyl, COOH or CHO groups to give $CH_2$ OH groups.

A reduction of the pyridinium salts of the formula VII (wherein Q is

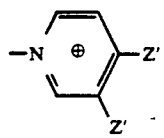

An⁻ and An is preferably Cl, Br or $CH_3SO_3$) to give compounds of the formula I can be effected, for example, by means of $NaBH_4$ in water, methanol or ethanol or in mixtures of these solvents, if desired with the addition of a base, such as NaOH, at temperatures between about 0° and 80°.

N-Benzyl groups can be split off by reduction by means of sodium in liquid ammonia.

It is also possible to reduce one or more carbonyl groups to $CH_2$ groups by the Wolff-Kishner method, for example by treatment with anhydrous hydrazine in absolute ethanol under pressure at temperatures between about 150° and 250°. Sodium alcoholate is advantageously used as a catalyst. The reduction can also be varied in accordance with the Huang-Minlon method, by carrying out the reaction with hydrazine hydrate in a high-boiling, water-miscible solvent, such as diethylene glycol or triethylene glycol, in the presence of an alkali, such as sodium hydroxide. As a rule, the reaction mixture is boiled for about 3-4 hours. The water is then removed by distillation, and the resulting hydrazone is decomposed at temperatures up to about 200°. The Wolff-Kishner reduction can also be carried out at room temperature in dimethyl sulfoxide using hydrazine.

Compounds which in other respects correspond to the formula I, but contain one or more solvolyzable group(s) instead of one or more H atoms, can be solvolyzed in particular hydrolyzed to give the compounds of the formula I.

The starting materials for the solvolysis can be obtained, for example, by reacting IIIa with compounds which correspond to the formula II ($X^1=X$), but contain one or more solvolyzable group(s) instead of one or more H atoms. Thus it is possible, in particular, to hydrolyze, for example in an acid medium, or, better, in a neutral or alkaline medium and at temperatures between 0° and 200°, 4-, 5-, 6- or 7-cyanoindole derivatives to give the corresponding 4-, 5-, 6- or 7-carbamoylindole derivatives or to hydrolyze 4-, 5-, 6- or 7-carboxyindole derivatives of the formula I or 1-acylindole derivatives (corresponding to the formula I, but containing, in the 1-position of the Ind radical, an acyl group, preferably an alkanoyl, alkylsulfonyl or arylsulfonyl group having in each case up to 10 C atoms, such as methanesulfonyl, benzenesulfonyl or p-toluenesulfonyl) to give the corresponding indole derivatives which are unsubstituted in the 1-position of the indole ring.

The basic catalysts used are preferably sodium hydroxide or carbonate, potassium hydroxide or carbonate or calcium hydroxide or ammonia. The selected solvent is preferably water; lower alcohols, such as methanol or ethanol; ethers, such as THF or dioxane; sulfones, such as tetramethylene sulfone; or mixtures thereof, preferably mixtures containing water. Hydroylsis can also be carried out merely by treatment with water alone, particularly at the boil.

Indole derivatives of the formula I A=—$CH_2$—S—$CH_2CH_2$—) can also be obtained by reacting Mannich bases of the formula IV with thiols of the formula V (or salts thereof).

Some of the starting materials of the formulae IV and V are known; those of the starting materials which are not known can readily be prepared analogously to the known compounds. Thus the Mannich bases of the formula IV can be obtained, for example, from indoles of the formula Ind-H, formaldehyde and amines of the formula $HN(R)_2$, and the thiols of the formula V can be obtained from the bases of the formula IIIa and thiol derivatives of the formula HS—$CH_2CH_2$—$X^1$ (it being also possible to protect the HS group intermediately).

Specifically, the reaction of IV with V is carried out in the presence or absence of an inert solvent at temperatures between about −20° and 250°, preferably between 60° and 150°. Examples of suitable solvents are hydrocarbons, such as benzene, toluene, xylenes or mesitylene; tertiary bases, such as triethylamine; pyridine or picolines; alcohols, such as methanol, ethanol or butanol; glycols and glycol ethers, such as ethylene glycol, diethylene glycol or 2-methoxyethanol; ketones, such as acetone; ethers, such as THF or dioxane; amides, such as DMF; or sulfoxides, such as dimethyl sulfoxide. Mixtures of these solvents are also suitable. The thiols of the formula V are preferably first converted into the corresponding mercaptides, preferably into the corresponding sodium or potassium mercaptides by reaction with sodium hydroxide or ethylate or potassium hydroxide or ethylate.

Compounds of the formula I are also obtained by eliminating HE from compounds of the formula VI, with the formation of a double bond. Depending on the definition of E, this can be, for example, an elimination of hydrogen halide, water (dehydration), a carboxylic acid of another acid, ammonia or HCN. The starting materials of the formula VI can be obtained, for example, by reacting II ($X^1=X$) with a compound of the formula IX

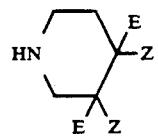

IX wherein E and Z have the meanings indicated.

If one of the radicals E is Hal, this substituent can be eliminated readily under basic reaction conditions. The following bases can be used: alkali metal hydroxides, alkali metal carbonates, alcoholates, such as, for example, potassium tert.-butylate, or amines, such as, for example, dimethylaniline, pyridine, collidine or quinoline; examples of solvents used are benzene, toluene, cyclohexane, THF or tert.-butanol. The amines used as bases can also be employed in an excess as solvents. If one of the radicals E is an OH group, it is preferable to use acids, such as acetic acid or hydrochloric acid or mixtures of both, as dehydrating agents. It can be advantageous to add a solvent (for example water or ethanol). Elimination of acyl, alkylsulfonyl and alkoxysulfonyloxy or amino radicals can be carried out under similar conditions. A gentle elimination of sulfonic acid radicals, for example those of mesylates or tosylates, is effected by boiling in DMF or dimethyl sulfoxide with alkali metal carbonates, for example $Li_2CO_3$, or with potassium acetate. Ammonia can be eliminated merely by heating the salts of the corresponding amino compounds (in particular the 4-amino derivatives). HCN can be eliminated similarly from compounds of the formula VI (one group E is CN) by heating. The elimination of HE from VI is generally effected at temperatures between 0° and about 250°, preferably between 50° and 200°.

It is also possible, if desired, to convert a compound of the formula I into another compound of the formula I by methods which are in themselves known.

Thus, in a thioether of the formula I (A=—$CH_2$—S—$CH_2CH_2$—), the thioether group can be oxidized to give an SO group or an $SO_2$ group, or, in a sulfoxide of the formula I (A=—$CH_2$—SO—$CH_2CH_2$—), the SO group can be oxidized to give an $SO_2$ group. If it is desired to obtain the sulfoxide, oxidation is carried out with, for example, hydrogen peroxide, per-acids, such as m-chloroperbenzoic acid, Cr(VI) compounds, such as chromic acid, KMnO$_4$, 1-chlorobenztriazole, Ce(VI) compounds, such as (NH$_4$)$_2$Ce(NO$_3$)$_6$, aromatic diazonium salts containing negative substituents, such as o-nitrophenyldiazonium or p-nitrophenyldiazonium chloride, or electrolytically, under relatively mild conditions and at relatively low temperatures (about $-80°$ to $+100°$). If, on the other hand, it is desired to obtain the sulfones (from the thioethers or the sulfoxides), the same oxidizing agents are used under more vigorous conditions and/or in excess and, as a rule, at higher temperatures. The customary inert solvents can be present or absent in these reactions. Examples of suitable inert solvents are water, aqueous mineral acids, aqueous alkali metal hydroxide solutions, lower alcohols, such as methanol or ethanol, esters, such as ethyl acetate, ketones, such as acetone, lower carboxylic acids, such as acetic acid, nitriles, such as acetonitrile, hydrocarbons, such as benzene, or chlorinated hydrocarbons, such as chloroform or CCL$_4$. A preferred oxidizing agent is 30% aqueous hydrogen peroxide. If it is used in the calculated amount in solvents such as acetic acid, acetone, methanol, ethanol or aqueous sodium hydroxide solution at temperatures between $-20°$ and $100°$, this oxidizing agent gives the sulfoxides, while in excess, at higher temperatures, preferably in acetic acid or in a mixture of acetic acid and acetic anhydride, it gives the sulfones.

Ethers of the formula I in which the radicals Ind and/or Ar are monosubstituted or disubstituted by O-alkyl can be split, whereupon the corresponding hydroxy derivatives are formed. For example, the ethers can be split by treatment with the dimethyl sulfide/boron tribromide complex, for example in toluene, ethers, such as THF, or dimethyl sulfoxide, or by fusing with hydrohalides of pyridine or aniline, preferably pyridine hydrochloride, at about 150°-250°, or by treatment with diisobutylaluminum hydride in toluene at about 0°-110°.

COW groups can also be converted into other COW groups by methods which are in themselves known. Thus it is possible to oxidize aldehyde groups to give carboxyl groups, for example by means of MnO$_2$ in an inert solvent, such as methyulene dichloride. On the other hand, carboxyl groups can be reduced, for example by means of diisobutylaluminium hydride in toluene. Carboxyl groups can be esterified, for example by treatment with alcohols in the presence of an acid catalyst, or by reaction with diazoalkanes. Converting the carboxylic acids into their chlorides, for example by means of SOCl$_2$, and subsequently reacting the product with NH$_3$ or amines results in the corresponding carboxamides, which can also be obtained by treating the carboxylic acid esters with ammonia or amines. Solvolysis of the esters or amides, preferably hydrolysis under the conditions indicated above, results in the carboxylic acids; in particular, carboxylic acids can be obtained from the carbamoyl compounds by treating the latter with NaOH or KOH in aqueous glycols or glycol ethers, for example diethylene glycol monomethyl or monoethyl ether, preferably at temperatures between about 50° and about 200°.

Reduction of COW groups, in particular formyl, alkoxycarbonyl or carboxyl groups, can also result in hydroxymethyl groups. It is preferable to use a complex hydride, such as LiAlH$_4$; aldehydes and esters can also be reduced by means of other reducing agents out of those listed above. It is preferable to carry out the reaction under the conditions indicated above. Conversely, hydroxymethyl groups can be oxidized to give formyl or carboxyl groups, for example by means of MnO$_2$ or CrO$_3$ or derivatives thereof.

The resulting base of the formula I can be converted into the appropriate acid addition salt by means of an acid. Acids which afford physiologically acceptable salts are suitable for this reaction. Thus it is possible to use inorganic acids, for example sulfuric acid, hydrogen halide acids, such as hydrochloric acid or hydrobromic acid, phosphoric acids, such as orthophosphoric acid, nitric acid or sulfamic acid, and also organic acids, specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicyclic acid, 2-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids and laurylsulfuric acid.

The free bases of the formula I can, if desired, be liberated from their salts by treatment with strong bases, such as sodium hydroxide or carbonate or potassium hydroxide or carbonate.

The invention also relates to the use of the compounds of the formula I and their physiologically acceptable salts for the preparation of pharmaceutical formulations, especially by a non-chemical route. In this connection, they can be brought into a suitable dosage form together with at least one excipient or auxiliary and, if appropriate, in combination with one or more further active compound(s), e.g., by bringing it together with at least one solid, liquid or semi-liquid carrier or auxiliary and, if appropriate, in combination with one or more further active compounds.

The invention also relates to agents, especially pharmaceutical formulations, containing at least one compound of the formula I and/or one of its physiologically acceptable salts. These formulations can be employed as medicaments in human or veterinary medicine. Suitable excipients are organic or inorganic substances which are suitable for enteral (for example oral) or parenteral administration or for topical application and which do not react with the new compounds, for example water, vegetable oils, benzyl alcohols, polyethylene glycols, gelatine, carbohydrates, such as lactose or starch, magnesium stearate, talc or petroleum jelly. Tablets, coated tablets, capsules, syrups, elixirs, drops or suppositories, in particular, are used for enteral administration, solutions, preferably oily or aqueous solutions, and also suspensions, emulsions or implants are used for parenteral administration, while ointments, creams or powders are used for topical application. The new compounds can also be lyophilized, and the resulting lyophilizates can be used, for example, for the preparation of injection formulations.

The formulations indicated can be sterilized and/or can contain auxiliaries, such as lubricants, preservatives, stabilizers and/or wetting agents, emulsifiers, salts for influencing the osmotic pressure, buffer substances, colorants, flavoring substances and/or aroma generating substances. If desired, they can also contain one or more further active compounds, for example one or more vitamins.

The invention also relates to the use of the compounds of the formula I and their physiologically acceptable salts in the therapeutic treatment of the human or animal (e.g., mammal) body and in combating diseases, in particular Parkinson's disease, extrapyramidal disorders in neuroleptic therapy, depressions and/or psychoses and side effects in the treatment of hypertension (for example by means of α-methyldopa). The compounds can also be used in endocrinology and gynaecology, for example for the therapy of acromegalia, hypogonadism, secondary amenorrhoea, premenstrual syndrome, undesirable puerperal lactation and generally as a prolactin inhibitor, and also for the therapy of cerebral disorders (for example migrane), particularly in geriatrics, in a manner similar to that of certain ergot alkaloids, and also for lowering the blood pressure.

In this respect, the substances according to the invention are, as a rule, administered analogously to known, commercially available formulations (for example bromocriptin or dihydroergocornin), preferably in dosages of about 0.2 to 500 mg, in particular about 0.2 to 50 mg, per dosage unit. The daily dosage is preferably about 0.001 to 10 mg/kg of body weight. The low dosages (about 0.2 to 1 mg per dosage unit; about 0.01 to 0.005 mg/kg of body weight) are particularly suitable in this respect for use as migraine agents; for the other indications dosages of 10 to 50 mg per dosage unit are preferred. More specifically, preferred dosage ranges for specific indications are as follows: parkinsonism 1 to 200, preferably 40 to 100; dyskinesia 40 to 100; psychosis, e.g., chronic shcizophrenia 2 to 20; acromegaly 2 to 50 mg per dosage unit. The particular dose for each specific patient depends, however, on a very wide variety of factors, for example on the effectiveness of the particular compound employed, on age, body weight, general state of health, sex, diet, periods and means of administration, the rate of excretion, the combination of medicaments and the severity of the particular disease to which the therapy relates. Oral administration is preferred.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples below, "customary working up" means as follows: if necessary, water is added, the mixture is extracted with methylene dichloride, the phases are separated, the organic phase is dried over sodium sulfate and filtered and evaporated and the residue is purified by chromatography over silica gel and/or by crystallization.

EXAMPLE 1

A solution of 28.4 g of methyl 3-(4-chloro-2-thiabutyl)-indole-5-carboxylate [or 32.8 g of methyl 3-(4-bromo-2-thiabutyl)-indole-5-carboxylate; obtainable by reacting methyl gramine-5-carboxylate with 2-mercaptoethanol to give methyl 3-(4-hydroxy-2-thiabutyl)-indole-5-carboxylate and subsequently reacting the latter with $SOCl_2$ or $PBr_3$] and 16 g of 4-phenyl-1,2,3,6-tetrahydropyridine in 100 ml of acetonitrile is stirred for 12 hours at 20° and is worked up in the customary manner to give methyl 3-[4-(4-phenyl-1,2,3,6-tetrahydropyridyl)-2-thiabutyl]-indole-5-carboxylate ("P"); hydrochloride, m.p. 202°-203°.

The following are obtained analogously from the corresponding starting materials of the formulae II and III;

3-[4-(4-phenyl-1,2,3,6-tetrahydropyridyl)-butyl]-5-hydroxymethylindole, m.p. 178°, 3-[4-(4-phenyl-1,2,3,6-tetrahydropyridyl)-2-thiabutyl]-4-hydroxymethylindole, 3-[4-(4-phenyl-1,2,3,6-tetrahydropyridyl)-2-thiabutyl]-5hydroxymethylindole, m.p. 118°-120°, 3-[4-(4-phenyl-1,2,3,6-tetrahydropyridyl)-2-thiabutyl]-6-bydroxymethylindole, m.p. 142°-143°, 3-[4-(4-phenyl-1,2,3,6-tetrahydropyridyl)-2-thiabutyl]-7-hydroxymethylindole, 3-[4-(4-phenyl-1,2,3,6-tetrahydropyridyl)-2-thiabutyl]-4-methoxycarbonylindole, 3-[4-(4-phenyl-1,2,3,6-tetrahydropyridyl)-2-thiabutyl]-6-methoxycarbonylindole, 3-[4-(4-phenyl-1,2,3,6-tetrahydropyridyl)-2-thiabutyl]-7-methoxycarbonylindole, 3-[4-(4-phenyl-1,2,3,6-tetrahydropyridyl)-2-thiabutyl]-4-ethoxycarbonylindole, 3-[4-(4-phenyl-1,2,3,6-tetrahydropyridyl)-2-thiabutyl]-5-ethoxycarbonylindole, 3-[4-(4-phenyl-1,2,3,6-tetrahydropyridyl)-2-thiabutyl]-6-ethoxycarbonylindole, m.p. 127°-129° and 3-[4-(4-phenyl-1,2,3,6-tetrahydropyridyl)-2-thiabutyl]-7-ethoxycarbonylindole.

EXAMPLE 2

A mixture of 2.64 g of methyl 3-(4-amino-2-thiabutyl)-indole-5-carboxylate [obtainable by reacting methyl 3-(4-bromo-2-thiabutyl)-indole-5-carboxylate with potassium phthalimide and subsequent hydrolysis] and 2.15 g of 1,5-dichloro-3-phenyl-2-pentene (obtainable by reducing diethyl 3-phenyl-2-pentene-1,5-dioate with $LiAlH_4$ and subsequently reacting the product with $SOCl_2$) in 40 ml of acetone and 40 ml of water is boiled for 24 hours and worked up in the customary manner. This gives "P", hydrochloride, m.p. 202°-203°.

EXAMPLE 3

A suspension of 41.6 g of methyl 3-[4-(4-phenyl-1,2,3,6-tetrahydropyridyl)-1,4-dioxobutyl]-indole-5-carboxylate [m.p. 218°; obtainable from 4-(5-methoxycarbonyl-3-indole)-4-oxobutyric acid and 4-phenyl-1,2,3,6- tetrahydropyridine] in 3 liters of hot absolute THF is added dropwise, with stirring, to a suspension of 23.4 g of LiAlH₄ in 1,100 ml of absolute THF, the mixture is boiled for 1 hour and cooled and the product is decomposed with water and sodium hydroxide solution and worked up in the customary manner. This gives 3-[4-(4-phenyl-1,2,3,6-tetrahydropyridyl)-butyl]-5-hydroxymethylindole, m.p. 178°.

From the corresponding dioxo esters, for example:
methyl 3-[4-(4-phenyl-1,2,3,6-tetrahydropyridyl)-1,4-dioxobutyl]-indole-4-carboxylate, m.p. 228°,
methyl 3-[4-(4-phenyl-1,2,3,6-tetrahydropyridyl)-1,4-dioxobutyl]-indole-6-carboxylate, m.p. 237° and
methyl 3-]4-(4-phenyl-1,2,3,6-tetrahydropyridyl)-1,4-dioxobutyl]-indole-7-carboxylate, m.p. 208°, the following can be obtained analogously:
3-[4-(4-phenyl-1,2,3,6-tetrahydropyridyl)-butyl]-4-hydroxymethylindole, m.p. 183°-184°,
3-[4-(4-phenyl-1,2,3,6-tetrahydropyridyl)-butyl]-6-hydroxymethylindole, m.p. 179° and
3-[4-(4-phenyl-1,2,3,6-tetrahydropyridyl)-butyl]-7-hydroxymethylindole, m.p. 178°.

The following is obtained analogously from 3-[4-oxo-4-(4-phenyl-1,2,3,6-tetrahydropyridyl)-butyl]-indole-2-carboxylic acid by means of LiAlH₄ in THF: 3-[4-(4-phenyl-1,2,3,6-tetrahydropyridyl)-butyl]-indole-2-carboxylic acid, m.p. 206°-208°.

EXAMPLE 4

1 g of NaBH₄ in 20 ml of water is added, with stirring, to a solution of 4.51 g of 1-[4-(5-carboxy-3-indolyl)-butyl]-4-phenylpyridinium bromide [obtainable from 3-(4-bromobutyl)-indole-5-carboxylic acid and 4-phenylpyridine] in 50 ml of 1N NaOH, and stirring is continued for a further 3 hours at 60°. Working up in the customary manner gives 3-[4-(4-phenyl-1,2,3,6-tetrahydropyridyl)-butyl]-indole-5-carboxylic acid, m.p. 284°-285°.

EXAMPLE 5

A mixture of 35.5 g of 3-[4-(4-phenyl-1,2,3,6-tetrahydropyridyl)-butyl]-5-cyanoindole [m.p. 167°; obtainable from the corresponding 5-formyl compound via the oxime], 27.1 g of NaOH, 520 ml of water and 420 ml of diethylene glycol monoethyl ether is stirred for 3 hours at a bath temperature of 140°. The mixture is cooled and worked up in the customary manner to give 3-[4-(4-phenyl-1,2,3,6-tetrahydropyridyl)-butyl]-indole-5-carboxamide, m.p. 200°-205°.

The following are obtained analogously by hydrolyzing the corresponding nitriles:
3-[2-(4-phenyl-1,2,3,6-tetrahydropyridyl)-ethyl]-indole-5-carboxamide,
3-[3-(4-phenyl-1,2,3,6-tetrahydropyridyl)-propyl]-indole-5-carboxamide,
3-[4-(4-phenyl-1,2,3,6-tetrahydropyridyl)-butyl]-indole-4carboxamide,
3-[4-(4-phenyl-1,2,3,6-tetrahydropyridyl)-butyl]-indole-6-carboxamide, m.p. 226°,
3-[4-(4-phenyl-1,2,3,6-tetrahydropyridyl)-butyl]-indole-7-carboxamide, m.p. 203°,
3-[4-(4-phenyl-1,2,3,6-tetrahydropyridyl)-butyl]-5-methoxyindole-6-carboxamide,
3-[4-(4-phenyl-1,2,3,6-tetrahydropyridyl)-butyl]-5-hydroxyindole-6-carboxamide,
3-[4-(4-phenyl-1,2,3,6-tetrahydropyridyl)-butyl]-7-chloroindole-4-carboxamide,
3-[4-(4-m-hydroxyphenyl-1,2,3,6-tetrahydropyridyl)-butyl]-indole-5-carboxamide,
3-[4-(4-p-hydroxyphenyl-1,2,3,6-tetrahydropyridyl)-butyl]-indole-5-carboxamide,
3-[5-(4-phenyl-1,2,3,6-tetrahydropyridyl)-pentyl]-indole-5-carboxamide,
3-[4-(3-phenyl-1,2,3,6-tetrahydropyridyl)-butyl]-indole-5-carboxamide,
3-[4-(3-m-hydroxyphenyl-1,2,3,6-tetrahydropyridyl)-butyl]-indole-5-carboxamide,
3-[4-(3-m-hydroxyphenyl-1,2,3,6-tetrahydropyridyl)-butyl]-indole-6-carboxamide,
3-[4-(3-p-hydroxyphenyl-1,2,3,6-tetrahydropyridyl)-butyl]-indole-5-carboxamide,
3-[4-(3-p-hydroxyphenyl-1,2,3,6-tetrahydropyridyl)-butyl]-indole-6-carboxamide,
3-[4-(4-phenyl-1,2,3,6-tetrahydropyridyl)-2-thiabutyl]-indole-4-carboxamide,
3-[4-(4-phenyl-1,2,3,6-tetrahydropyridyl)-2-thiabutyl]-indole-5-carboxamide,
3-[4-(4-phenyl-1,2,3,6-tetrahydropyridyl)-2-thiabutyl]-indole-6-carboxamide,
3-[4-(4-phenyl-1,2,3,6-tetrahydropyridyl)-2-thiabutyl]-indole-7-carboxamide,
3-[4-(4-phenyl-1,2,3,6-tetrahydropyridyl)-2-thiabutyl]-5-methoxyindole-6-carboxamide,
3-[4-(4-phenyl-1,2,3,6-tetrahydropyridyl)-2-thiabutyl]-5-hydroxyindole-6-carboxamide,
3-[4-(4-phenyl-1,2,3,6-tetrahydropyridyl)-2-thiabutyl]-7-chloroindole-4-carboxamide,
3-[4-(4-m-hydroxyphenyl-1,2,3,6-tetrahydropyridyl)-2-thiabutyl]-indole-5-carboxamide,
3-[4-(4-p-hydroxyphenyl-1,2,3,6-tetrahydropyridyl)-2-thiabutyl]-indole-5-carboxamide,
3-[4-(3-m-hydroxyphenyl-1,2,3,6-tetrahydropyridyl)-2-thiabutyl]-indole-5-carboxamide,
3-[4-(3-m-hydroxyphenyl-1,2,3,6-tetrahydropyridyl)-2-thiabutyl]-indole-6-carboxamide,
3-[4-(3-p-hydroxyphenyl-1,2,3,6-tetrahydropyridyl)-2-thiabutyl]-indole-5-carboxamide,
3-[4-(3-p-hydroxyphenyl-1,2,3,6-tetrahydropyridyl)-2-thiabutyl]-indole-6-carboxamide,
3-[4-(4-phenylpiperidino)-butyl]-indole-5-carboxamide,
3-[4-(4-phenylpiperidino)-butyl]-indole-6-carboxamide,
3-[4-(4-m-hydroxyphenylpiperidino)-butyl]-indole-5-carboxamide,
3-[4-(4-m-hydroxyphenylpiperidino)-butyl]-indole-6-carboxamide,
3-[4-(4-p-hydroxyphenylpiperidino)-butyl]-indole-5-carboxamide,
3-[4-(4-p-hydroxyphenylpiperidino)-butyl]-indole-6-carboxamide,
3-[4-(3-m-hydroxyphenylpiperidino)-butyl]-indole-5-carboxamide,
3-[4-(3-m-hydroxyphenylpiperidino)-butyl]-indole-6-carboxamide,
3-[4-(3-p-hydroxyphenylpiperidino)-butyl]-indole-5-carboxamide,
3-[4-(3-p-hydroxyphenylpiperidino)-butyl]-indole-6-carboxamide,
3-[4-(4-phenylpiperidino)-2-thiabutyl]-indole-5-carboxamide,
3-[4-(4-phenylpiperidino)-2-thiabutyl]-indole-6-carboxamide,
3-[4-(4-m-hydroxyphenylpiperidino)-2-thiabutyl]-indole-5-carboxamide, 3-[4-(4-m-hydroxyphenylpiperidino)-2-thiabutyl]-indole-6-carboxamide, 3-[4-(4-p-hydroxyphenylpiperidino)-2-thiabutyl]-indole-5-carboxamide, 3-[4-(4-p-hydroxyphenylpiperidino)-2-thiabutyl]-indole-6-carboxamide, 3-[4-(3-m-hydroxyphenylpiperidino)-2-thiabutyl]-indole-5-carboxamide, 3-[4-(3-m-hydroxyphenylpiperidino)-2-thiabutyl]-indole-6-carboxamide, 3-[4-(3-p-hydroxyphenylpiperidino)-2-thiabutyl]-indole-5-carboxamide and 3-[4-(3-p-hydroxyphenylpiperidino)-2-thiabutyl]-indole-6-carboxamide,

EXAMPLE 6

The reaction is carried out as described in Example 5, but the mixture is boiled for 16 hours and, after working up in the customary manner, gives 3-[4-(4-phenyl-1,2,3,6-tetrahydropyridyl)-butyl]-indole-5-carboxylic acid, m.p. 284°-285°.

The following are obtained analogously by hydrolyzing the corresponding nitriles:

3-[2-(4-phenyl-1,2,3,6-tetrahydropyridyl)-ethyl]-indole-5-carboxylic acid,

3-[3-(4-phenyl-1,2,3,6-tetrahydropyridyl)-propyl]-indole-5-carboxylic acid,

3-[3-(4-phenyl-1,2,3,6-tetrahydropyridyl)-propyl]-indole-5-carboxylic acid,

3-[4-(4-phenyl-1,2,3,6-tetrahydropyridyl)-butyl]-indole-4-carboxylic acid,

3-[4-(4-phenyl-1,2,3,6-tetrahydropyridyl)-butyl]-indole-6-carboxylic acid, m.p. 268°, 3-[4-(4-phenyl-1,2,3,6-tetrahydropyridyl)-butyl]-indole-7-carboxylic acid, m.p. 262°-265°, 3-[4-(4-phenyl-1,2,3,6-tetrahydropyridyl)-butyl]-5-methoxyindole-6-carboxylic acid, 3-[4-(4-phenyl-1,2,3,6-tetrahydropyridyl)-butyl]-5-hydroxyindole-6-carboxylic acid, 3-[4-(4-phenyl-1,2,3,6-tetrahydropyridyl)-butyl]-7-chloroindole-4-carboxylic acid, m.p. 263°-266°

3-[4-(4-o-methoxyphenyl-1,2,3,6-tetrahydropyridyl)-butyl]-indole-5-carboxylic acid, 3-[4-(4-m-methoxyphenyl-1,2,3,6-tetrahydropyridyl)-butyl]-indole-5-carboxylic acid, 3-[4-(4-p-methoxyphenyl-1,2,3,6-tetrahydropyridyl)-butyl]-indole-5-carboxylic acid, 3-[4-(4-o-hydroxyphenyl-1,2,3,6-tetrahydropyridyl)-butyl]-indole-5-carboxylic acid, 3-[4-(4-m-hydroxyphenyl-1,2,3,6-tetrahydropyridyl)-butyl]-indole-5-carboxylic acid, 3-[4-(4-p-hydroxyphenyl-1,2,3,6-tetrahydropyridyl)-butyl]-indole-5-carboxylic acid, 3-[4-(4-(3-methoxy-4-hydroxyphenyl-1,2,3,6-tetrahydropyridyl)-butyl]-indole-5-carboxylic acid, 3-[4-(4-(3,4-dimethoxyphenyl-1,2,3,6-tetrahydropyridyl)-butyl]-indole-5-carboxylic acid, 3-[4-(4-(3,4-methylenedioxyphenyl-1,2,3,6-tetrahydropyridyl)-butyl]-indole-5-carboxylic acid, 3-[4-(4-(2-thienyl)-1,2,3,6-tetrahydropyridyl)-butyl]-indole-5-carboxylic acid, 3-[4-(4-(3-thienyl)-1,2,3,6-tetrahydropyridyl)-butyl]-indole-5-carboxylic acid, 3-[5-(4-phenyl-1,2,3,6-tetrahydropyridyl)-pentyl]-indole-5-carboxylic acid, 3-[4-(3-phenyl-1,2,3,6-tetrahydropyridyl)-butyl]-indole-5-carboxylic acid, 3-[4-(3-p-methoxyphenyl-1,2,3,6-tetrahydropyridyl)-butyl]-indole-5-carboxylic acid, 3-[4-(3-m-hydroxyphenyl-1,2,3,6-tetrahydropyridyl)-butyl]-indole-5-carboxylic acid, 3-[4-(3-m-hydroxyphenyl-1,2,3,6-tetrahydropyridyl)-butyl]-indole-6-carboxylic acid, 3-[4-(3-p-hydroxyphenyl-1,2,3,6-tetrahydropyridyl)-butyl]-indole-5-carboxylic acid, 3-[4-(3-hydroxyphenyl-1,2,3,6-tetrahydropyridyl)-butyl]-indole-6-carboxylic acid, 3-[4-(4-phenylpiperidino)-butyl]-indole-5-carboxylic acid, 3-[4-(4-phenylpiperidino)-butyl]-indole-6-carboxylic acid, 3-[4-(4-m-hydroxyphenylpiperidino)-butyl]-indole-5-carboxylic acid, 3-[4-(4-m-hydroxyphenylpiperidino)-butyl]-indole-6-carboxylic acid, 3-[4-(4-p-hydroxyphenylpiperidino)-butyl]-indole-5-carboxylic acid, 3-[4-(4-p-hydroxyphenylpiperidino)-butyl]-indole-6-carboxylic acid, 3-[4-(3-m-hydroxyphenylpiperidino)-butyl]-indole-5-carboxylic acid, 3-[4-(4-p-hydroxyphenylpiperidino)-butyl]-indole-6-carboxylic acid, 3-[4-(3-p-hydroxyphenylpiperidino)-butyl]-indole-5-carboxylic acid, 3-[4-(3-p-hydroxyphenylpiperidino)-butyl]-indole-6-carboxylic acid, 3-[4-(4-phenylpiperidino)-butyl]-7-chloroindole-4-carboxylic acid and 3-[4-(3-m-hydroxyphenylpiperidino)-butyl]-7-chloroindole-4-carboxylic acid.

EXAMPLE 7

4.68 g of methyl 1-benzenesulfonyl-3-[4-(4-phenyl-1,2,3,6-tetrahydropyridyl)-butyl]-indole-5-carboxylate [obtainable from methyl 1-benzenesulfonyl-3-(4-chlorobutyl)-indole-5-carboxylate and 4-phenyl-1,2,3,6-tetrahydropyridine] are boiled with 1 g of KOH in 7 ml of water and 14 ml of ethanol for 16 hours, and the mixture is concentrated and worked up in the customary manner to give 3-[4-(4-phenyl-1,2,3,6-tetrahydropyridyl)-butyl]-indole-5-carboxylic acid, m.p. 284°-285°.

EXAMPLE 8

2.76 g of Na are dissolved in 180 ml of ethanol, 21.9 g of 1-(2-mercaptoethyl)-4-phenyl-1,2,3,6-tetrahydropyridine [obtainable by reacting 4-phenyl-1,2,3,6-tetrahydropyridine with thioglycolic acid to give 1-(2-mercaptoacetyl)-4-phenyl-1,2,3,6-tetrahydropyridine and reducing the latter with LiAlH$_4$ and 23.2 g of methyl gramine-5-carboxylate are added, the mixture is boiled for 16 hours and evaporated, and the residue is worked up in the customary manner to give "P", hydrochloride, m.p. 202°-203°.

The following are obtained analogously from the corresponding starting materials of the formulae IV and V:

methyl 3-[4-(4-phenyl-1,2,3,6-tetrahydropyridyl)-2-thiabutyl]-5-methoxyindole-6-carboxylate, ethyl 3-[4-(4-phenyl-1,2,3,6-tetrahydropyridyl)-2-thiabutyl]-5-methoxyindole-6-carboxylate, hydrochloride, m.p. 169°-173°, methyl 3-[4-(4-phenyl-1,2,3,6-tetrahydropyridyl)-2-thiabutyl]-5-hydroxyindole-6-carboxylate, ethyl 3-[4-(4-phenyl-1,2,3,6-tetrahydropyridyl)-2-thiabutyl]-5-hydroxyindole-6-carboxylate and methyl 3-[4-(4-phenyl-1,2,3,6-tetrahydropyridyl)-2-thiabutyl]-7-chloroindole-4-carboxylate.

EXAMPLE 9

4.05 g of 1-methyl-3-[4-(4-hydroxy-4-phenyl-1-piperidyl)-butyl]-indole-5-carboxamide [obtainable by reacting 1-methyl-3-(4-bromobutyl)-indole-5carboxamide with 4-piperidone, followed by reaction with $C_6H_5Li$ and hydrolysis] are heated at 50° with 40 ml of hydrochloric acid for 2 hours, and the mixture is worked up in the customary manner to give 1-methyl-3-[4-(4-phenyl-1,2,3,6-tetrahydropyridyl)-butyl]-indole-5-carboxamide.

EXAMPLE 10

6 ml of 30% $H_2O_2$ are added to a boiling solution of 4.06 g of "P" in 50 ml of ethanol, and the mixture is then boiled for 3 hours. After a further 4 ml of the oxidizing agent have been added, the mixture is boiled for a further 9 hours and is cooled and worked up in the customary manner to give methyl 3-[4-(4-phenyl-1,2,3,6-tetrahydropyridyl)-2-thiabutyl]-indole-5-carboxylate-S-oxide.

EXAMPLE 11

9 ml of 30% $H_2O_2$ are added to a solution of 4.06 g of "P" in 20 ml of acetic acid, and the mixture is boiled for 90 minutes. Working up in the customary manner gives methyl 3-[4-(4-phenyl-1,2,3,6-tetrahydropyridyl)-2-thiabutyl]-indole-5-carboxylate-S,S, -dioxide.

EXAMPLE 12

A mixture of 4.04 g of 3-[4-(4-p-methoxyphenyl-1,2,3,6-tetrahydropyridyl)-butyl]-indole-5-carboxylic acid and 3.5 g of pyridine hydrochloride is stirred for 3 hours at 160°. Working up in the customary manner gives 3-[4-(4-p-hydroxyphenyl-1,2,3,6-tetrahydropyridyl)-butyl]-indole-5-carboxylic acid.

EXAMPLE 13

36 g of 3-[4-(4-phenyl-1,2,3,6-tetrahydropyridyl)-butyl]-5-hydroxymethylindole are dissolved in 1.6 liters of THF, and 300 ml of ether are added. 55 g of $MnO_2$ are added with stirring. The mixture is stirred for 16 hours at 20°, a further 100 g of $MnO_2$ are added in portions, and stirring is continued for a further 100 hours at 20°. Filtration and working up in the customary manner gives 3-[4-(4-phenyl-1,2,3,6-tetrahydropyridyl)-butyl]-5-formylindole, m.p. 131°.

The following are obtained analogously by oxidizing the corresponding hydroxymethylindoles:

3-[4-(4-phenyl-1,2,3,6-tetrahydropyridyl)-butyl]-2-formylindole, m.p. 129°-130°, 3-[4-(4-phenyl-1,2,3,6-tetrahydropyridyl)-butyl]-4-formylindole, 3-[4-(4-phenyl-1,2,3,6-tetrahydropyridyl)-butyl]-6-formylindole, 3-[4-(4-phenyl-1,2,3,6-tetrahydropyridyl)-butyl]-7-formylindole, 3-[4-(4-phenyl-1,2,3,6-tetrahydropyridyl)-2-thiabutyl]-4-formylindole, 3-[4-(4-phenyl-1,2,3,6-tetrahydropyridyl)-2-thiabutyl]-5-formylindole, 3-[4-(4-phenyl-1,2,3,6-tetrahydropyridyl)-2-thiabutyl]-5-formylindole and 3-[4-(4-phenyl-1,2,3,6-tetrahydropyridyl)-2-thiabutyl]-7-formylindole.

EXAMPLE 14

3.9 g of 3-[4-(4-phenyl-1,2,3,6-tetrahydropyridyl)-butyl]-6-hydroxymethylindole are dissolved in 50 ml of methylene dichloride, 9 g of $MnO_2$ are added to the solution, the mixture is stirred for 60 hours at 40° and the insoluble components are filtered off. Working up the filtrate in the customary manner gives 3-[4-(4-phenyl-1,2,3,6-tetrahydropyridyl)-butyl]-indole-6-carboxylic acid, m.p. 268°.

EXAMPLE 15

3.88 g of 3-[4-(4-phenyl-1,2,3,6-tetrahydropyridyl)-butyl]-5-formylindole are dissolved in 80 ml of methylene dichloride, 9 g of $MnO_2$ are added, and the suspension is stirred for 48 hours at 40°. Filtration and working up in the customary manner give 3-[4-(4-phenyl-1,2,3,6-tetrahydropyridyl)-butyl]-indole-5-carboxylic acid, m.p. 284°-285°.

EXAMPLE 16

4.04 g of 3-[4-(4-phenyl-1,2,3,6-tetrahydropyridyl)-butyl]-indole-5-carboxylic acid are suspended in 25 ml of toluene, and a 3-fold molar amount of a 20% strength solution of diisobutylaluminum hydride in toluene is added dropwise, under $N_2$ and with stirring, the mixture is boiled for 2 hours and cooled and is decomposed with water, and the product is worked up in the customary manner to give 3-[4-(4-phenyl-1,2,3,6-tetrahydropyridyl)-butyl]-5-formylindole, m.p. 131°.

EXAMPLE 17

A solution of 4.04 g of 3-[4-(4-phenyl-1,2,3,6-tetrahydropyridyl)-butyl]-indole-5-carboxylic acid in 40 ml of THF is added dropwise, with stirring and under $N_2$, to a suspension of 0.76 g of lithium aluminum hydride in 30 ml of THF. The mixture is stirred for a further 2 hours at 20°, is decomposed with dilute sodium hydroxide solution and then with water and is filtered. The filtrate is worked up in the customary manner. This gives 3-[4-(4-phenyl-1,2,3,6-tetrahydropyridyl)-butyl]-6-hydroxymethylindole, m.p. 178°.

EXAMPLE 18

A solution of 4.18 g of methyl 3-[4-(4-phenyl-1,2,3,6-tetrahydropyridyl)-butyl]-indole-5-carboxylate in 40 ml of THF is added dropwise, with stirring and under $N_2$, to a suspension of 0.57 g of lithium aluminum hydride in 20 ml of THF. The mixture is stirred for 1 hour at 20° and is decomposed with dilute sodium hydroxide solution and then with water and is filtered, and the filtrate is worked up in the customary manner to give 3-[4-(4-phenyl-1,2,3,6-tetrahydropyridyl)-butyl]-5-hydroxymethylindole, m.p. 178°.

The hydroxymethyl compounds mentioned in Example 3 and also 2-hydroxymethyl-3-[4-(4-phenyl-1,2,3,6-tetrahydropyridyl)-butyl]-indole, m.p. 162°-163.5° are obtained analogously from the corresponding esters.

EXAMPLE 19

A solution of 3.88 g of 3-[4-(4-phenyl-1,2,3,6-tetrahydropyridyl)-butyl]-5-formylindole in 40 ml of THF is added dropwise, under $N_2$ and with stirring, to a suspension of 0.57 g of lithium aluminum hydride in 20 ml of THF. The mixture is stirred for a further hour at 20° and is decomposed with dilute sodium hydroxide solution and then with water and is filtered and worked up in the customary manner to give 3-[4-(4-phenyl-1,2,3,6-tetrahydropyridyl)-butyl]-5-hydroxymethylindole, m.p. 178°.

EXAMPLE 20

HCl is passed into a boiling solution of 4.04 g of 3-[4-(4-phenyl-1,2,3,6-tetrahydropyridyl)-butyl]-indole-5-carboxylic acid in 50 ml of absolute ethanol for 2 hours. The mixture is boiled for a further hour and worked up in the customary manner to give ethyl 3-[4-(4-phenyl-1,2,3,6-tetrahydropyridyl)-butyl]-indole-5-carboxylate. Rf 0.65 (silica gel; 8:2 $CH_2Cl_2/CH_3OH$).

The following are obtained analogously by esterification:

methyl 3-[4-(4-phenyl-1,2,3,6-tetrahydropyridyl)-butyl]-indole-2-carboxylate, m.p. 114.5°-115.5°, methyl 3-[4-(4-phenyl-1,2,3,6-tetrahydropyridyl)-butyl]-indole-4-carboxylate, methyl 3-[4-(4-phenyl-1,2,3,6-tetrahydropyridyl)-butyl]-indole-5-carboxylate, methyl 3-[4-(4-phenyl-1,2,3,6-tetrahydropyridyl)-butyl]-indole-6-carboxylate, methyl 3-[4-(4-phenyl-1,2,3,6-tetrahydropyridyl)-butyl]-indole-7-carboxylate, ethyl 3-[4-(4-phenyl-1,2,3,6-tetrahydropyridyl)-butyl]-indole-2-carboxylate, ethyl 3-[4-(4-phenyl-1,2,3,6-tetrahydropyridyl)-butyl]-indole-4-carboxylate, ethyl 3-[4-(4-phenyl-1,2,3,6-tetrahydropyridyl)-butyl]-indole-6-carboxylate, ethyl 3-[4-(4-phenyl-1,2,3,6-tetrahydropyridyl)-butyl]-indole-7-carboxylate, methyl 3-[4-(4-phenyl-1,2,3,6-tetrahydropyridyl)-butyl]-5-methoxyindole-6-carboxylate, ethyl 3-[4-(4-phenyl-1,2,3,6-tetrahydropyridyl)-butyl]-5-methoxyindole-6-carboxylate, methyl 3-[4-(4-phenyl-1,2,3,6-tetrahydropyridyl)-butyl]-5-hydroxyindole-6-carboxylate, ethyl 3-[4-(4-phenyl-1,2,3,6-tetrahydropyridyl)-butyl]-5-hydroxyindole-6-carboxylate, methyl 3-[4-(4-phenyl-1,2,3,6-tetrahydropyridyl)-butyl]-7-chloroindole-4-carboxylate, hydrochloride, m.p. 219°-221° ethyl 3-[4-(4-phenyl-1,2,3,6-tetrahydropyridyl)-butyl]-7-chloroindole-4-carboxylate and butyl 3-[4-(4-phenyl-1,2,3,6-tetrahydropyridyl)-butyl]-indole-5-carboxylate.

EXAMPLE 21

4.04 g of 3-[4-(4-phenyl-1,2,3,6-tetrahydropyridyl)-butyl]-indole-5-carboxylic acid are dissolved in 30 ml of chloroform, the solution is saturated with HCl gas, 1.8 g of thionyl chloride are added dropwise and the mixture is boiled for 2 hours. After evaporation, 30 ml of toluene are added and the mixture is evaporated again. The residue is dissolved in 20 ml of chloroform, this solution is added dropwise, with stirring, to a saturated solution of ammonia in 50 ml of chloroform, the mixture is stirred for 2 hours at 20° and is filtered, and the filtrate is concentrated. Working up in the customary manner gives 3-[4-(4-phenyl-1,2,3,6-tetrahydropyridyl)-butyl]-indole-5-carboxamide, m.p. 207°-208°.

The following are obtained analogously from the acids by reacting the latter with $SOCl_2$ and then with ammonia or the corresponding amines:

3-[4-(4-phenyl-1,2,3,6-tetrahydropyridyl)-butyl]-indole-2-carboxamide,

3-[4-(4-phenyl-1,2,3,6-tetrahydropyridyl)-butyl]-indole-2-carboxylic acid N-methylamide and 3-[4-(4-phenyl-1,2,3,6-tetrahydropyridyl)-butyl]-indole-2-carboxylic acid N,N-dimethylamide. Rf 0.72 (silica gel, 8:2 $CH_2Cl_2/CH_3OH$).

EXAMPLE 22

0.02 mol of concentrated ammonia (D=0.9) is added dropwise at 20° to a solution of 4.18 g of methyl 3-[4-(4-phenyl-1,2,3,6-tetrahydropyridyl)-butyl]-indole-5-carboxylate in 30 ml of dimethylformamide. The mixture is stirred for a further hour at 20° and worked up in the customary manner to give 3-[4-(4-phenyl-1,2,3,6-tetrahydropyridyl)-butyl]-indole-5-carboxamide, m.p. 207°-208°.

EXAMPLE 23

A mixture of 37.3 g of 3-[4-(4-phenyl-1,2,3,6tetrahydropyridyl)-butyl]-5-carbamoylindole, 27.1 g of NaOH, 525 ml of water and 450 ml of diethylene glycol monoethyl ether is boiled with stirring for 16 hours. The mixture is cooled, worked up in the customary manner and acidified to give 3-[4-(4-phenyl-1,2,3,6-tetrahydropyridyl)-butyl]-indole-5-carboxylic acid, m.p. 284°-285°.

EXAMPLE 24

4.5 g of 3-[4-(4-phenyl-1,2,3,6-tetrahydropyridyl)-2-thiabutyl]-5-methoxy-6-ethoxycarbonylindole are boiled with 20 ml of water and 100 ml of 2N ethanolic KOH for 30 minutes, and the mixture is worked up in the customary manner to give 3-[4-(4-phenyl-1,2,3,6-tetrahydropyridyl)-2-thiabutyl]-5-methoxyindole-6-carboxylic acid, m.p. 168°-171°.

The following are obtained analogously by saponifying the corresponding methyl or ethyl esters:

3-[4-(4-phenyl-1,2,3,6-tetrahydropyridyl)-2-thiabutyl]-indole-4-carboxylic acid, 3-[4-(4-phenyl-1,2,3,6-tetrahydropyridyl)-2-thiabutyl]-indole-5-carboxylic acid, m.p. 184°-189°, 3-[4-(4-phenyl-1,2,3,6-tetrahydropyridyl)-2-thiabutyl]-indole-6-carboxylic acid, 3-[4-(4-phenyl-1,2,3,6-tetrahydropyridyl)-2-thiabutyl]-indole-7-carboxylic acid, 3-[4-(4-phenyl-1,2,3,6-tetrahydropyridyl)-2-thiabutyl]-5-hydroxyindole-6-carboxylic acid, 3-[4-(4-phenyl-1,2,3,6-tetrahydropyridyl)-2-thiabutyl]-7-chloroindole-4-carboxylic acid, 3-[4-(4-m-hydroxyphenyl-1,2,3,6-tetrahydropyridyl)-2-thiabutyl]-indole-5-carboxylic acid, 3-[4-(4-p-hydroxyphenyl-1,2,3,6-tetrahydropyridyl)-2-thiabutyl]-indole-5-carboxylic acid, 3-[4-(3-m-hydroxyphenyl-1,2,3,6-tetrahydropyridyl)-2-thiabutyl]-indole-5-carboxylic acid, 3-[4-(3-m-hydroxyphenyl-1,2,3,6-tetrahydropyridyl)-2-thiabutyl]-indole-6-carboxylic acid, 3-[4-(3-p-hydroxyphenyl-1,2,3,6-tetrahydropyridyl)-2-thiabutyl]-indole-5-carboxylic acid, 3-[4-(3-p-hydroxyphenyl-1,2,3,6-tetrahydropyridyl)-2-thiabutyl]-indole-6-carboxylic acid, 3-[4-(4-phenylpiperidino)-butyl]-indole-5-carboxylic acid, 3-[4-(4-phenylpiperidino)-butyl]-indole-6-carboxylic acid, 3-[4-(4-m-hydroxyphenylpiperidino)-butyl]-indole-5-carboxylic acid, 3-[4-(4-m-hydroxyphenylpiperidino)-butyl]-indole-6-carboxylic acid, 3-[4-(4-p-hydroxyphenylpiperidino)-butyl]-indole-5-carboxylic acid, 3-[4-(4-p-hydroxyphenylpiperidino)-butyl]-indole-6-carboxylic acid, 3-[4-(3-m-hydroxyphenylpiperidino)-butyl]-indole-5-carboxylic acid, 3-[4-(3-m-hydroxyphenylpiperidino)-butyl]-indole-6-carboxylic acid, 3-[4-(3-m-hydroxyphenylpiperidino)-2-thiabutyl]-7-chloroindole-4-carboxylic acid, 3-[4-(3-p-hydroxyphenylpiperidino)-2-thiabutyl]-7-chloroindole-5-carboxylic acid and 3-[4-(3-p-hydroxyphenylpiperidino)-2-thiabutyl]-7-chloroindole-6-carboxylic acid.

EXAMPLE 25

In analogy to Example 1, the following are obtained from the corresponding starting materials of formula II and III:

3-[3-(4-phenyl-1,2,3,6-tetrahydropyridyl)-propyl]-4-hydroxymethyl-indole, m.p. 164°–168°

2-hydroxymethyl-3-[4-(4-phenyl-1,2,3,6-tetrahydropyridyl)-butyl]-5-methoxyindole, m.p. 145°–146°

2-hydroxymethyl-3-[4-(4-phenyl-1,2,3,6-tetrahydropyridyl)-butyl]-6-methoxyindole.

EXAMPLE 26

In analogy to Example 3, there are obtained from the corresponding oxo-carboxylic acids:

3-[2-(4-phenyl-1,2,3,6-tetrahydropyridyl)-ethyl]-indole-6-carboxylic acid, m.p. >240°

3-[3-(4-phenyl-1,2,3,6-tetrahydropyridyl)-propyl]-indole-4-carboxylic acid, m.p. 268°–271°

3-[4-(4-phenyl-1,2,3,6-tetrahydropyridyl)-butyl]-5-hydroxyindole-6-carboxylic acid 3-[4-(4-phenyl-1,2,3,6-tetrahydropyridyl)-butyl]-6-hydroxyindole-5-carboxylic acid 3-[4-(4-phenyl-1,2,3,6-tetrahydropyridyl)-2-thiabutyl]-5-hydroxy-indole-6-carboxylic acid 3-[4-(4-phenyl-1,2,3,6-tetrahydropyridyl)-2-thiabutyl]-6-hydroxy-indole-5-carboxylic acid.

EXAMPLE 27

In analogy to Example 8 there is obtained from 1-(2-mercaptoethyl)-3-m-hydroxyphenyl-piperidine and 5-hydroxymethyl-gramine:

3-[4-(3-m-hydroxyphenyl-piperidino)-2-thiabutyl]-5-hydroxymethyl-indole.

EXAMPLE 28

A solution of 1.5 g of diisobutylaluminiumhydride in 15 ml of toluene is added with cooling and stirring to a suspension of 3.9 g of 2-hydroxymethyl-3-[4-(4-phenyl-1,2,3,6-tetrahydropyridyl)-butyl]-6-methoxy-indole in 400 ml of toluene. The mixture is warmed to room temperature, refluxed for 3 hours with stirring, cooled and worked up in the usual manner. 2-Hydroxymethyl-3-[4-(4-phenyl-1,2,3,6-tetrahydropyridyl)-butyl]-6-hydroxy-indole is obtained.

From the corresponding 5-methoxy compound there is obtained analogously:

2-hydroxymethyl-3-[4-(4-phenyl-1,2,3,6-tetrahydropyridyl)-butyl]-5-hydroxy-indole.

EXAMPLE 29 a) A mixture of 127.2 g of methyl-3-(4-chlorobutyl)-indole-5-carboxylate [m.p. 99°–100°; obtainable by reaction of 3-methyl-4-nitrobenzoic acid with N,N-dimethylformamide-dimethylacetal in pyrrolidine/DMF to yield instable 3-(2-dimethylaminovinyl)-4-nitrobenzoic acid (m.p. 105°–107°), treatment with $H_2$/5%-Pd-C in toluene at room temperature and atmospheric pressure to yield methyl indole-5-carboxylate (m.p. 120°–124°), reaction with 4-chloro-butyryl chloride/$AlCl_3$ in dichloromethane to yield methyl 3-(4-chloro-1-oxobutyl)-indole-5-carboxylate (m.p. 197°–199°) and reduction with $NaBH_4$/$BF_3$-etherate in THF below 45°], 96 g of 4-phenyl-1,2,3,6-tetrahydropyridine and 144 ml of triethylamine is refluxed for 3 hours. Thereafter, 800 ml of acetonitrile are added and the mixture is heated until a clear solution is formed. On cooling, methyl 3-[4-(4-phenyl-1,2,3,6-tetrahydropyridyl)-butyl]-indole-5-carboxylate precipitates which is filtered and recrystallized from ethanol; m.p. 145°.

b) The obtained ester (200 g) is dissolved in 2.4 l of boiling dioxane. Two l of hot aqueous 1n NaOH solution are added, the solution is refluxed for 30 minutes, cooled and filtered. A precipitate of 3-[4-(4-phenyl-1,2,3,6-tetrahydropyridyl)-butyl]-indole-5-carboxylic acid hydrochloride is formed on the addition of 2.5 l of aqueous 1n HCl; this is filtered, washed with water, acetone and ether and finally dried at 80°, m.p. 298°–299°.

The examples below relate to pharmaceutical formulations containing amines of the formula I or acid addition salts thereof:

Example A: Tablets

A mixture of 1 kg of 3-[4-(4-phenyl-1,2,3,6-tetrahydropyridyl)-butyl]-indole-5-carboxamide, 4 kg of lactose, 1.2 kg of potato starch, 0.2 kg of talc and 0.1 kg of magnesium stearate is compressed in the customary manner to give tablets, so that each tablet contains 10 mg of active compound.

Example B: Coated tablets

Tablets are compressed analogously to Example A and are then coated in a customary manner with a coating composed of sucrose, potato starch, talc, tragacanth and colorant.

Example C: Capsules 2 kg of 3-[4-(4-phenyl-1,2,3,6-tetrahydropyridyl)-butyl]-indole-5-carboxylic acid are filled into hard gelatine capsules in a customary manner, so that each capsule contains 20 mg of the active compound.

Example D: Ampoules

A solution of 1 kg of 3-[4-(4-phenyl-1,2,3,6-tetrahydropyridyl)-butyl]-5-methoxyindole-6-carboxylic acid hydrochloride in 60 liters of twice distilled water is filtered under sterile conditions and is filled into ampoules, which are lyophilised under sterile conditions and closed in a sterile manner. Each ampoule contains 10 mg of active compound.

Tablets, coated tablets, capsules and ampoules containing one or more of the other active compounds of the formula I and/or physiologically acceptable acid addition salts thereof can be obtained analogously.

The preceding examples can be repeated with similar success by substituting the generically or specifically described reactants and/or operating conditions of this invention for those used int he preceding examples.

From the foregoing description, one skilled in the art can easily ascertain the essential characteristics of this invention, and without departing from the spirit and

What is claimed is:

1. An indole compound of the formula

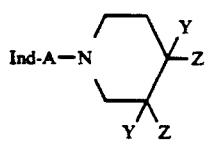

wherein
Ind is 5-carboxyindol-3-yl or 5-carbamoylindol-3-yl,
A is —(CH₂)₄— or —CH₂—S—CH₂CH₂—,
the two Y groups together are a C-C bond, one Z is Ar, and the other Z is H, and
Ar is phenyl in the 4-position,
or a physiologically acceptable acid addition salt thereof.

2. 3-[4-(4-Phenyl-1,2,3,6-tetrahydropyridyl)-butyl]-indole-5-carboxylic acid.

3. 3-[4-(4-Phenyl-1,2,3,6-tetrahydropyridyl)-butyl]-indole-5-carboxamide.

4. A pharmaceutical composition comprising a compound of claim 1 and a pharmaceutically acceptable carrier.

5. A pharmaceutical composition comprising about 0.2 to about 500 mg of a compound of claim 2 and a pharmaceutically acceptable carrier.

6. A pharmaceutical composition comprising a compound of claim 2 and a pharmaceutically acceptable carrier.

7. A pharmaceutical composition comprising a compound of claim 3 and a pharmaceutically acceptable carrier.

8. A method of treating Parkinson's disease in a patient in need of such treatment, comprising administering to the patient an effective amount of a compound of claim 1.

9. A method of treating hypertension, comprising administering to a mammal in need of anti-hypertensive treatment a hypotensive amount of an indole compound of the formula

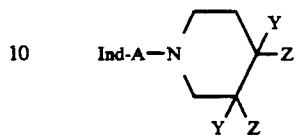

wherein
Ind is indol-3-yl substituted by hydroxymethyl or —COW, or indol-3-yl substituted by hydroxymethyl or —COW, and monosubstituted or disubstituted by alkyl, Oalkyl, OH, F, Cl or Br,
W is H, OH, Oalkyl, NH₂, NHalkyl or N(alkyl)₂,
A is —(CH₂)ₙ—, —CH₂—S—CH₂CH₂—, —CH₂SO—CH₂CH₂— or —CH₂—SO₂—CH₂CH₂—,
n is 2, 3, 4 or 5,
the two Y groups are each H or together are a C-C bond, one Z is Ar, and the other Z is H, and
Ar is phenyl, 2-thienyl, 3-thienyl or phenyl monosubstituted or disubstituted by O-alkyl or OH, or substituted by methylenedioxy,
wherein each of the alkyl groups has 1-4 C atoms, with the proviso that when n is 2 or 3, the hydroxymethyl or COW group is in the 4-, 5-, 6- or 7-position of the indol-3-yl radical, or a physiologically acceptable acid addition salt thereof.

10. A method of treating hypertension, comprising administering to a mammal in need of anti-hypertensive treatment a hypotensive amount of a compound of claim 2.

11. A method of treating hypertension, comprising administering to a mammal in need of anti-hypertensive treatment a hypotensive amount of a compound of claim 3.

* * * * *